(12) United States Patent
Schattenmann

(10) Patent No.: US 6,455,721 B1
(45) Date of Patent: Sep. 24, 2002

(54) METHOD FOR MAKING ORGANYLTRIORGANOOXYSILANES

(75) Inventor: Florian Johannes Schattenmann, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/951,219

(22) Filed: Sep. 14, 2001

(51) Int. Cl.⁷ .............................. C07F 7/08; C07F 7/18
(52) U.S. Cl. ...................................... 556/478; 556/482
(58) Field of Search ................................ 556/478, 482

(56) References Cited

U.S. PATENT DOCUMENTS 2,380,995 A    8/1945  Rochow

FOREIGN PATENT DOCUMENTS

DE    3821483    6/1988

OTHER PUBLICATIONS

Bazant et al., "Organosilicon Compounds", vol. 2, part 1, Academic Press, NY, 1965, p. 109.*

"Preparation of Diorganodialkoxysilanes"—Juergen Graefe et al.—Abstract—Jan. 1998.

"The Direct Synthesis of Organosilicon Compounds", Eugene G. Rochow, Jan. 29, 1945, pp. 963–965.

"A Silicate Substitution Route to Organosilicon Compounds", George B. Goodwin et al.—1990, Americal Chemical Society, pp. 251–263.

* cited by examiner

Primary Examiner—Paul F. Shaver
(74) Attorney, Agent, or Firm—Bernadette M. Bennett; Noreen C. Johnson

(57) ABSTRACT

A method for the preparation of organyltriorganooxysilanes containing at least one silicon-carbon bond is provided comprising reacting at least one tetraorganooxysilane with an activated carbon and at least one base.

19 Claims, No Drawings

METHOD FOR MAKING ORGANYLTRIORGANOOXYSILANES

STATEMENT REGARDING FEDERALLY SPONSORED RESEARCH & DEVELOPMENT

The government may have certain rights in this invention pursuant to contract number DE-FC02-98CH10931 awarded by the United States Department of Energy.

BACKGROUND OF THE INVENTION

The present invention relates to a method for making organyltriorganooxysilanes. More particularly, the present invention relates to a process involving the reaction of a tetraorganooxysilane with activated carbon in the presence of a base.

Organyltriorganooxysilanes are silicon-containing compounds of the formula $RSi(OR)_3$ where each R independently represents a monovalent hydrocarbon group such as an alkyl group, aryl group, aralkyl group, alkaryl group, cycloalkyl group, or bicycloalkyl group. Silicon-containing compounds with silicon-carbon bonds, such as organyltriorganooxysilanes, are commonly made from silicon dioxide via elemental silicon or from a compound containing a silicon-hydrogen bond.

The process commonly used commercially for the production of silicones and more particularly, alkoxysilanes, is a two-step process. The first step is described in Rochow, U.S. Pat. No. 2,380,995 where silicon is reacted with methylchloride to form a methylchlorosilane. The second step involves the reaction of the methylchlorosilane with an alcohol to produce the alkoxysilane. The two-step process uses silicon, also referred to as elemental silicon, as a starting material. To prepare elemental silicon, silicon dioxide must be reduced. It is well known in the art that the silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicones from silicon dioxide using the aforementioned two-step process is expensive and not energy efficient.

In the past, the synthesis of silicon-containing compounds with silicon-carbon bonds has relied heavily on the reduction of silicon dioxide to elemental silicon. Unfortunately, the large amount of energy needed for synthesizing silicones such as organyltriorganooxysilanes from silicon dioxide can be problematic. Thus, new synthetic routes are constantly being sought which can form silicon-carbon bonds.

SUMMARY OF THE INVENTION

The present invention provides a method for the preparation of organyltriorganooxysilanes containing at least one silicon-carbon bond comprising reacting at least one tetraorganooxysilane with activated carbon in the presence of at least one base.

DETAILED DESCRIPTION OF THE INVENTION

The present invention relates to a process involving the reaction of at least one tetraorganooxysilane with activated carbon in the presence of at least one base to form an organyltriorganooxysilane containing at least one silicon-carbon bond. Tetraorganooxysilanes are of the formula $(RO)_4Si$ where each R independently represents a monovalent hydrocarbon group such as an alkyl group, aryl group, aralkyl group, alkaryl group, cycloalkyl group, or bicycloalkyl group. The term "alkyl group" is intended to designate both normal alkyl and branched alkyl groups. Normal and branched alkyl groups are preferably those containing carbon atoms in a range between about 1 and about 22, and include as illustrative non-limiting examples methyl, ethyl, propyl, isopropyl, butyl, tertiary-butyl, pentyl, neopentyl, hexyl, octyl, decyl, dodecyl. Aryl groups include an example such as phenyl. Cyclo- or bicycloalkyl groups represented are preferably those containing ring carbon atoms in a range between about 3 and about 12 with a total number of carbon atoms less than or equal to about 50. Some illustrative non-limiting examples of cycloalkyl groups include cyclobutyl, cyclopentyl, cyclohexyl, methylcyclohexyl, and cycloheptyl. Preferred aralkyl groups are those containing carbon atoms in a range between about 7 and about 14; these include, but are not limited to, benzyl, phenylbutyl, phenylpropyl, and phenylethyl. Typical tetraorganooxysilanes include tetraalkoxysilanes such as tetramethoxysilane, tetraethoxysilane, and tetraisopropoxysilane; tetraaryloxysilanes such as tetraphenoxysilane; as well as tetra(alkoxyaryloxy)silanes such as dimethoxydiphenoxysilane. Typically, the level of purity of the tetraorganooxysilane is at least about 80% by weight and preferably, about 95% by weight.

"Activated carbon" as used herein refers to an amorphous, highly absorbent form of carbon typically characterized by a large surface area. The activated carbon in the present invention typically has a surface area in a range between about 100 $m^2/g$ (square meters per gram) and about 1500 $m^2/g$ and more typically, in a range between about 400 $m^2/g$ and about 1000 $m^2/g$. Typically, the activated carbon is present in a mole ratio of activated carbon to tetraorganooxysilane in a range between about 1:10 and about 100:1, and more typically, a mole ration of activate carbon to tetraorganooxysilane in a range between about 1:5 and about 5:1.

Bases include, but are not limited to, metal hydroxides, metal amides, metal alkoxides, metal aryloxides, or combinations thereof. Typically, the base is sodium methoxide ($NaOCH_3$), potassium-tert-butoxide [$K-O-C(CH_3)_3$], or combinations thereof. Preferably, the base is sodium methoxide.

Organyltriorganooxysilanes are compounds of the formula $RSi(OR)_3$ where R is defined as above. Preferably, R is methyl or ethyl.

The reaction commonly can be practiced in a fixed bed reactor. The method for preparation of organyltriorganooxysilanes, however, can be performed in other types of reactors, such as fluidized bed reactors and stirred bed reactors. More specifically, the fixed bed reactor is a column that contains the activated carbon and base wherein a carrier gas, such as an inert gas of argon or helium, is passed through at a rate in a range between about 0.1 milliliters per minute (ml/min) and about 100 ml/min and preferably, in a range between about 0.5 ml/min and about 30 ml/min. The tetraorganooxysilane is typically fed into the carrier gas stream. A stirred bed is similar to a fixed bed in which there is mechanical agitation of some sort in order to keep the bed in constant motion. A fluidized bed reactor, on the other hand, is a bed comprising activated carbon and base which is fluidized; that is, the activated carbon and base are suspended in the gas, typically argon, that is passed through the reactor. Reaction typically occurs at a temperature in a range between about 50° C. and about 600° C. and commonly, in a range between about 200° C. and about 450° C.

The reaction of the present invention can be performed in batch mode, continuous mode, or semi-continuous mode.

With a batch mode reaction, for instance, all of the reactant components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants.

The tetraorganooxysilane is typically added to the reactor via any convenient method to provide batch, continuous, or semi-continuous means of addition. A pumping device, such as a motor driven syringe, is an example of a continuous means of addition. A motor driven syringe allows for consistent amounts of tetraorganooxysilane to be added to the reaction mixture at given time intervals. Addition of the tetraorganooxysilane via a motor driven syringe is illustrative and non-limiting. Manual injection is also a common method for the addition of tetraorganooxysilanes. Typically, the tetraorganooxysilane is added at a rate in a range between about 0.1 milliliters per hour (ml/h) and about 10 ml/h, and preferably, in a range between about 0.5 ml/h and about 2.1 ml/h. The tetraorganooxysilane is typically added in a mole ratio of base to tetraorganooxysilane in a range between about 10:1 and about 1:100 and commonly, a mole ratio of base to tetraorganooxysilane in a range between about 5:1 and 1:10. The reaction is typically at about atmospheric pressure.

Products in the organyltriorganooxysilane synthesis may be isolated by any convenient means. Typically, product(s) may be isolated by condensation into fractions typically referred to as condensate. Products may be purified by any convenient means such as distillation. Once the fractions are collected, the formation of the organyltriorganooxysilane may be confirmed by such methods as gas chromatography (GC), gas chromatography-mass spectroscopy (GC/MS), and proton nuclear magnetic resonance spectroscopy ($^1$H-NMR), carbon nuclear magnetic resonance spectroscopy ($^{13}$C-NMR) and silicon nuclear magnetic resonance spectroscopy ($^{29}$Si-NMR).

Organyltriorganooxysilanes obtained by the present method may be used in a wide variety of applications. For example, organyltriorganooxysilanes may be used as precursors to silicones and organofunctional silicon compounds, precursors to pure and ultra-pure silicon dioxide, coupling agents, additives for plastic applications, and adhesion promoters.

In order that those skilled in the art will be better able to practice the invention, the following examples are given by way of illustration and not by way of limitation.

EXAMPLE 1

Powdered activated Carbon (Darco® G-60, surface area= 900 m$^2$/g; 0.5 grams (g); 41.6 millimoles (mmol)) and sodium methoxide (NaOCH$_3$; 1.0 g; 18.5 mmol) were intimately mixed and charged into a fixed-bed flow reactor with vertical furnace and flushed with argon (5 milliliters per minute (ml/min)). The reactor was heated to 250° C. using argon as the carrier gas. Tetramethoxysilane (1.72 ml/hour; 11.7 mmol/h; 10 ml total) was fed into the argon stream (5 ml/min) using a motor driven syringe. The reactor effluent downstream was collected in fractions using a water-chilled condenser and methyltrimethoxysilane [MeSi(OMe)$_3$] formation was confirmed by gas chromatography and gas chromatography/mass spectroscopy. The reaction was carried out with a temperature ramp. After collecting a fraction, typically in a range between about 0.5 grams and about 2 grams, the reactor temperature was increased by 25° C. as indicated in Table 1. The temperature was ramped for screening purposes. The percentages of methyltrimethoxysilane refer to percentages of the individual samples downstream of the reactor including unreacted tetramethoxysilane. Results can be seen in Table 1.

TABLE 1

| Fraction | Weight of sample (g) | Temperature (° C.) | % MeSi(OMe)$_3$ |
|---|---|---|---|
| 1 | 1.97 | 250 | 0 |
| 2 | 1.08 | 275 | 0.6 |
| 3 | 0.87 | 300 | 1.0 |
| 4 | 0.62 | 325 | 1.1 |
| 5 | 1.11 | 350 | 0.7 |
| 6 | 1.27 | 375 | 0 |

EXAMPLE 2

The procedure of Example 1 was followed with the following modifications: the temperature was increased by 25° C. after the second fraction was taken. Results can be seen in Table 2.

TABLE 2

| Fraction | Weight of sample (g) | Temperature (° C.) | % MeSi(OMe)$_3$ |
|---|---|---|---|
| 1 | 1.54 | 250 | 0 |
| 2 | 1.69 | 250 | 0.3 |
| 3 | 1.21 | 275 | 0.9 |
| 4 | 1.08 | 300 | 0.8 |
| 5 | 1.89 | 356 | 0.3 |

EXAMPLE 3

The procedure of Example 1 was followed with the following source of activated carbon was Sibunit 2/5 (Boreskov Industrial surface area=417 m$^2$/g). Results can be seen in Table 3.

TABLE 3

| Fraction | Weight of sample (g) | Temperature (° C.) | % MeSi(OMe)$_3$ |
|---|---|---|---|
| 1 | 1.16 | 250 | 0 |
| 2 | 1.45 | 275 | 0 |
| 3 | 1.35 | 300 | 0.7 |
| 4 | 1.12 | 325 | 1.1 |
| 5 | 1.56 | 350 | 0.4 |
| 6 | 1.65 | 375 | 0 |

While typical embodiments have been set forth for the purpose of the foregoing description should not be deemed to be a limitation on the invention. Accordingly, various modifications, adaptations, and may occur to one skilled in the art without departing from the spirit and present invention.

What is claimed is:

1. A method for the preparation of organyltriorganooxysilanes containing at least one silicon-carbon bond comprising reacting at least one tetraorganooxysilane with an activated carbon and at least one base.

2. The method according to claim 1, wherein the tetraorganooxysilane comprises tetraalkoxysilanes, tetraaryloxysilanes, tetra(alkoxyaryloxy)silanes, or combinations thereof.

3. The method according to claim 2, wherein the tetraorganooxysilane comprises tetramethoxysilane.

4. The method according to claim 1, wherein the activated carbon has a surface area in a range between about 100 m$^2$/g and about 1500 m$^2$/g.

5. The method according to claim 4, wherein the activated carbon has a surface area in a range between about 400 m$^2$/g and about 1000 m$^2$/g.

6. The method according to claim 1, wherein the base comprises metal hydroxides, metal amides, metal alkoxides, metal aryloxides, or combinations thereof.

7. The method according to claim 6 wherein the base comprises sodium methoxide, potassium-tert-butoxide, or combinations thereof.

8. The method according to claim 7, wherein the base comprises sodium methoxide.

9. The method according to claim 1, wherein the reaction occurs in a reactor bed comprising a fixed bed reactor, a fluidized bed reactor, or a stirred bed reactor.

10. The method according to claim 9, wherein the reaction occurs in a fixed bed reactor.

11. The method according to claim 9, wherein the reaction is operated in batch mode.

12. The method according to claim 9, wherein the reaction is operated in continuous mode.

13. The method according to claim 1, wherein the reaction is conducted at a temperature in the range between about 50° C. and about 600° C.

14. The method according to claim 13, wherein the reaction is conducted at a temperature in a range between about 200° C. and about 450° C.

15. The method according to claim 1, wherein the base is present in a mole ratio of base to tetraorganooxysilane in a range between about 10:1 and about 1:100.

16. The method according to claim 15, wherein the base is present in a mole ratio of base to tetraorganooxysilane in a range between about 5:1 and about 1:10.

17. The method according to claim 1, wherein the activated carbon is present in a mole ratio of activated carbon to tetraorganooxysilane in a range between about 1:10 and about 100:1.

18. The method according to claim 17, wherein the activated carbon is present in a mole ratio of activated carbon to tetraorganooxysilane in a range between about 1:5 and about 5:1.

19. A method for the preparation of methyltrimethoxysilane comprising reacting tetramethoxysilane with activated carbon and sodium methoxide wherein the activated carbon is present in a mole ratio of activated carbon to tetraorganooxysilane in a range between about 1:5 and about 5:1 and has a surface area in a range between about 400 m$^2$/g and about 1000 m$^2$/g and wherein the sodium methoxide is present in a mole ratio of sodium methoxide to trimethoxysilane in a range between about 5:1 and about 1:10.

* * * * *